United States Patent [19]

Shiokawa et al.

[11] Patent Number: 4,882,344
[45] Date of Patent: Nov. 21, 1989

[54] PYRIDYLMETHYL-4-THIAZOLINES

[75] Inventors: Kozo Shiokawa, Kawasaki; Shinichi Tsuboi; Shoko Sasaki, both of Hino; Koichi Moriya, Tokyo; Yumi Hattori; Katsuhiko Shibuya, both of Hachioji, all of Japan

[73] Assignee: Nihon Tokushu Noyaku Seizo K.K., Tokyo, Japan

[21] Appl. No.: 243,545

[22] Filed: Sep. 13, 1988

Related U.S. Application Data

[62] Division of Ser. No. 88,932, Aug. 24, 1987, Pat. No. 4,803,277.

[30] Foreign Application Priority Data

Oct. 9, 1986 [JP] Japan .................. 61-211753

[51] Int. Cl.⁴ .................. C07D 417/06; A61K 31/44
[52] U.S. Cl. .................. 514/342; 546/280
[58] Field of Search .................. 514/342; 546/280

[56] References Cited

FOREIGN PATENT DOCUMENTS

| | | |
|---|---|---|
| 0136636 | 4/1985 | European Pat. Off. . |
| 0154178 | 9/1985 | European Pat. Off. . |
| 0163855 | 12/1985 | European Pat. Off. . |
| 0192060 | 8/1986 | European Pat. Off. . |
| 0199974 | 12/1986 | European Pat. Off. . |
| 0212600 | 3/1987 | European Pat. Off. . |

OTHER PUBLICATIONS

Pestic. Venom. Neurotox., 1976, pp. 153–158, "Nitromethylene heterocycles as insecticides".

*Primary Examiner*—Jane T. Fan

*Attorney, Agent, or Firm*—Sprung Horn Kramer & Woods

[57] ABSTRACT

Novel insecticidally active heterocyclic compounds of the formula

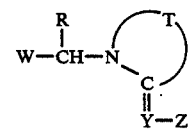

wherein
W represents a substituted pyridyl group, or a 5- or 6-membered optionally substituted heterocyclic group containing at least two hetero atoms selected from oxygen, sulfur and nitrogen atoms,
R represents a hydrogen atom or an alkyl group,
Y represents =N— or

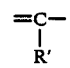

R' represents a hydrogen atom, an alkyl group, an aryl group, an acyl group, an alkoxycarbonyl group or a cyano group,
Z represents a nitro group or a cyano group, and
T represents 3 or 4 optionally substituted ring members of a 5- or 6-membered unsaturated heterocyclic ring which it forms together with the adjoining carbon atom and nitrogen atom, said 5- or 6-membered unsaturated heterocyclic ring containing 1 to 3 hetero atoms which are selected from oxygen, sulfur and nitrogen atoms and at least one of which is a nitrogen atom.

4 Claims, No Drawings

PYRIDYLMETHYL-4-THIAZOLINES

This is a division, of application Ser. No. 088,932, filed Aug. 24, 1987, now U.S. Pat. No. 4,803,277 issued Feb. 7, 1989.

The present invention relates to novel heterocyclic compounds, to a process for their preparation, and to their use as insecticides.

It has already been disclosed that certain pyridine resonance hybrids have insecticidal activities (see U.S. Pat. No. 3922 242) and that certain 1-substituted 1,2-dihydro-2-nitroimino pyridines have an anti-inflammatory activity (see J. Med. Chem., 1971, Vol. 14, No. 10, pp. 988–990).

There have now been found novel heterocyclic compounds of the formula (I)

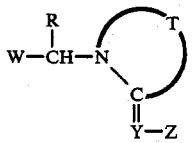

wherein

H represents a substituted pyridyl group or a 5- or 6-membered optionally substituted heterocyclic group which has at least two hetero atoms selected from oxygen, sulfur and nitrogen atoms.

R represents a hydrogen atom or an alkyl group,

Y represents =N- or

R' represents a hydrogen atom, an alkyl group, an aryl group, an acyl group, an alkoxycarbonyl group or a cyano group.

Z represents a nitro group or a cyano group, and

T represents 3 or 4 optionally substituted ring members of a 5- or 6- membered unsaturated heterocyclic ring which it forms together with the adjoining carbon atom and nitrogen atom, said 5- or 6-membered unsaturated heterocyclic ring containing 1 to 3 hetero atoms which are selected from oxygen, sulfur and nitrogen atoms and at least one of which is a nitrogen atom.

The compounds of the formula (I) are obtained by a process in which
(a) compounds of the formula (II)

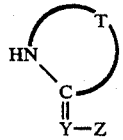

wherein Y, Z and T are as defined above, are reacted with compounds of the formula (III)

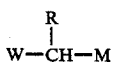

wherein R and W are as defined above, and M represents a halogen atom or the group —OSO$_2$—R' in which R' represents an alkyl or aryl group, in the presence of an inert solvent, if appropriate in the presence of a base.

The novel heterocyclic compounds of the formula (I) exhibit powerful insecticidal properties.

Surprisingly, the novel heterocyclic compounds according to the invention exhibit a substantially greater insecticidal action than compounds known from the aforesaid prior art, as shown in insecticidal test examples given hereinafter.

Among the compounds according to the invention, of the formula (I), preferred compounds are those in which W is a pyridyl group having at least one substituent selected from halogen atoms, $C_1$–$C_4$ alkyl groups optionally substituted by halogen, $C_1$–$C_4$ alkoxy groups optionally substituted by halogen, $C_2$–$C_4$ alkenyl groups optionally substituted by halogen, $C_1$–$C_4$ alkylsulfinyl groups, $C_1$–$C_4$ alkyl-sulfonyl groups and $C_3$–$C_4$ alkynyl groups, or a 5- or 6- membered heterocyclic group which contains two hetero atoms selected from oxygen, sulfur and nitrogen atoms, at least one of the hetero atoms being a nitrogen atom, and which may optionally by substituted by a substituent selected from halogen atoms, $C_1$–$C_4$ alkyl groups optionally substituted by halogen, $C_1$–$C_4$-alkoxy groups optionally substituted by halogen, $C_2$–$C_4$ alkenyl groups optionally substituted by halogen, $C_1$–$C_4$ alkylsulfinyl groups, $C_1$–$C_4$ alkylsulfonyl groups and $C_3$–$C_4$ alkynyl groups.

R represents a hydrogen atom or a methyl group,

Y represents =N—,

Z represents a nitro group or a cyano group, and

T represents 3 or 4 ring members of a 5- or 6-membered unsaturated heterocyclic ring which it forms together with the adjoining carbon atom and nitrogen atom, said 5- or 6-membered unsaturated heterocyclic ring containing 1 to 2 hetero atoms which are selected from sulfur and nitrogen atoms and at least one of which is a nitrogen atom, said 3 or 4 ring members being optionally substituted by at least one of halogen atoms and $C_1$–$C_4$ alkyl groups optionally substituted by halogen.

Very particularly preferred compounds of the formula (I) are those in which

W represents a pyridyl group having one substituent selected from fluoro, chloro, bromo, methyl, ethyl, trifluoromethyl, methoxy, trifluoromethoxy, vinyl, allyl, methylsulfinyl, methylsulfonyl and propargyl, or a 5-membered heterocyclic group containing one oxygen or sulfur atom and one nitrogen atom and optionally being substituted by one substituent selected from fluoro, chloro, bromo, methyl, ethyl, trifluoromethyl, methoxy, trifluoromethoxy, vinyl, allyl, methylsulfinyl, methylsulfonyl and propargyl, R represents a hydrogen atom or a methyl group, Y stands for =N—, Z represents a nitro group or a cyano group, and T represents 3 or 4 ring members of an imidazoline, thiazoline, dihydropyridine or dihydropyrimidine ring which it forms together with the adjoining carbon atom and nitrogen atom, the ring members being optionally substituted by chloro or methyl.

Specific examples of the compounds (I) of the invention include 1-(2-chloro-5-pyridylmethyl)-2-nitroimino-1,2-dihydropyridine, 1-(2-chloro-5-pyridylmethyl)-5-methyl-2-nitroimino-1,2-dihydropyridine, 1-(3-methyl-5-isoxazolylmethyl)-2-nitroimino-1,2-dihydropyridine, 3-(2-chloro-5-pyridylmethyl)-2-nitroimino-4-thiazoline, and 1-(2-chloro-5-pyridylmethyl)-2-cyanoimino-1,2-dihydropyridine.

When 2-nitroimino-1,2-dihydropyridine and 2-chloro-5-chloromethylpyridine are used as the starting materials in process (a), the reaction can be exemplified by the following scheme:

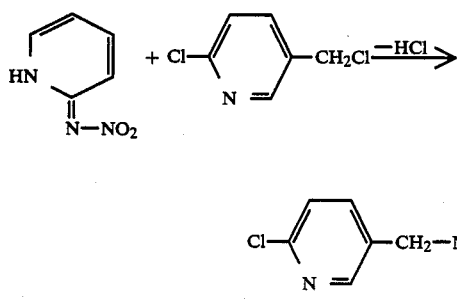

In process (a), the compound of formula (II) means one based on the above-given definitions of Y, Z and T.

In formula (II), Y, Z and T are preferably synonymous with the preferred definitions given above.

Formula (II) embraces both known and novel compounds.

The compound of formula (II) can exist in resonance structure as shown below:

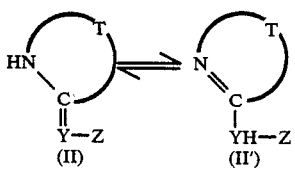

In view of the above resonance structure, examples of the known compounds of formula (II) include 2-nitromethylpyridine and its nuclearly alkyl-substituted products described in J. Am. Chem. Soc., vol. 91, pages 1856–1857; 4-nitromethylpyrimidine described in J. Org. Chem., vol. 37, pages 3662–3670; 3-nitromethyl-1,2,5-oxadiazole described in Liebigs Ann. Chem., 1975, pages 1029–1050; 2-pyridylacetonitrile described in J. Am. Chem Soc., vol. 73, pages 5752–5759; 5-imidazolylacetonitrile described in Chem. Abst., vol. 50, 15516a; 2-imidazolylacetonitrile described in J. Med. Chem., vol. 11, pages 1028–1031; 2-pyrimidylacetonitrile, 2-thiazolylacetonitrile and 4-thiazolylacetonitrile described in Japanese Laid-Open Patent Publication No. 49972/1974; 2-nitraminopyridine described in J. Med. Chem., vol. 14, pages 988–990; 5-chloro-2-nitraminopyridine described in Beilstein, 22II, page 519; methyl-substituted-2-nitraminopyridine described in J. Am. Chem. Soc., vol. 77, pages 3154–3155; 5-chloro-2-nitraminopyrimidine described in U.S. Pat. No. 3,041,339; 3-methyl-6-nitraminopyridazine and 3-nitraminopyridazine described in J. Chem. Soc., 1950, pages 3236–3239; 3-chloro-6-nitraminopyridazine described in Chem. Adst., vol. 55, 1634i; 2-nitraminothiazole described in Can. J. Chem., vol. 31, pages 885–893; 2-nitroimino-4-trifluoromethyl-thiazole described in J. Org. Chem., vol. 20, pages 499–510; methyl-substituted-2-nitraminothiazole described in Can. J. Chem., vol. 34, pages 1261–1270; 4-nitramino-1,2,3-thiadiazole described in J. Chem. Soc., 1965, page 5175; 3-methyl-5-nitramino-1,2,4-thiadiazole described in Belgian Pat. No. 619423; 2-alkyl or -halogen substituted-5-nitramino-1,3,4-thiadiazole described in J. Pharm. Soc. Japan, vol. 75, pages 1149–1150 or Japanese Patent Publication No. 9736/1977; 2-cyanaminopyridine described in Ann. Pharm. Fr., vol. 26, pages 469–472; 2-cyanomethylthiazole described in Chem. Pharm. Bull., vol. 21, pages 74–86; 2-cyanaminopyrimidine described in British Patent No. 860,423; and 2-dicyanomethylpyridine described in Chem. Ber., vol. 85, pages 397–407.

Ethyl 2-nitro-2-(2-pyridyl)acetate can be easily obtained by nitrating ethyl 2-pyridylacetate in accordance with the method described in J. Org. Chem., vol. 37, pages 3662–3670.

In process (a), the compound of formula (III) as another starting material means one based on the definitions of R, W and M.

In formula (III), R and W are preferably synonymous with the above-given preferred definitions, and M preferably represents chloro, bromo or tosyloxy.

The compounds of formula (III) are known, and typical examples are
2-chloro-5-chloromethylpyridine,
5-chloromethyl-3-methylisoxazole,
5-chloromethyl-2-chlorothiazole,
5-chloromethyl-2-methylthiazole,
5-chloromethyl-2-fluoropyridine,
2-bromo-5-chloromethylpyridine, and
5-chloromethyl-2-methylpyridine.

In effecting process (a), all inert organic solvents may be used as suitable diluents.

Examples of such diluents include water; aliphatic, alicyclic and aromatic hydrocarbons (optionally chlorinated) such as hexane, cyclohexane, petroleum ether, ligroin, benzene, toluene, xylene, methylene chloride, chloroform, carbon tetrachloride, ethylene chloride, and chlorobenzene; ethers such as diethyl ether, methyl ethyl ether, di-isopropyl ether, dibutyl ether, propylene oxide, dioxide and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

Examples of the base to be applied are inorganic bases such as sodium hydroxide and potassium carbonate and organic bases such as triethylamine.

Process (a) can be practiced over a wide temperature range, for example at a temperature of about 0° to 120° C., preferably from about 20° to about 80° C.

Preferably, the reaction is carried out under atmospheric pressure, but it is also possible to operate under elevated or reduced pressures.

In the practice of the above process, the desired compound of formula (I) can be obtained by reacting 1 mole of the compound of formula (II) with about 1.0 to 1.2 moles of triethylamine and about 1 to 1.2 moles, preferably 1 mole, of the compound of formula (III) in an inert solvent such as ethanol.

The compound of formula (I) of this invention can assume a resonance structure as shown below.

$$\underset{(I)}{\overset{R}{\underset{|}{W-CH-N}}\diagdown\overset{T}{\underset{Y-Z}{\overset{\|}{C}}}} \rightleftharpoons \underset{(I')}{\overset{R}{\underset{|}{W-CH-N^{\oplus}}}\diagdown\overset{T}{\underset{Y=Z^{\ominus}}{\overset{|}{C}}}}$$

When a terminal of T on the C side is a nitrogen atom, the compound of formula (I) can also take the following resonance structure:

$$\underset{(I'')}{\overset{R}{\underset{|}{W-CH-N}}\diagdown\overset{T}{\underset{HY-Z}{\overset{\|}{C}}}}$$

The active compounds are well tolerated by plants, have a favourable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus Asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera; for example *Blatta orientalis, Periplaneta americana, Leucphaea maderae, Blattella germanica, Acheta domesticus,* Gryllotalpa spp., *Locusta migrato ria migratorioides, Melanoplus differentialis* and *Schistocerca gregaria;* from the order of the Dermaptera, for example *Forficula auricularia;* from the order of the Isoptera, for example Recticulitermes spp.;

from the order of the Anoplura, for example *Phvlloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci,* from the order of the Heteroptera, for example Eurygaster spp., *Dysdercus intermedius, Piesma guadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis,* and *Costelytra zealandica;* from the order of the Hymenoptera for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;*

In the field of veterinary medicine, the novel compounds of this invention are effective against various noxious animal parasites (endo- and ecto-parasites) such as insects and worms.

Examples of such animal parasites are insects such as Gastrophilus spp., Stomoxys spp., Trichodectes spp., Rhodnius spp., and Ctenocephalides canis.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case water is used as an extender, organic solvents can, for example, also be used as auxiliary solvents.

As liquid solvents diluents or carriers, there are preferably suitable aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractioned natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 per cent by weight of active compound, preferably from 0.5 to 90 per cent by weight of active compound.

The active compounds according to the invention can be present in their commercially available formulations and in the use forms, prepared from these formulations, also in admixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, biologically active substances produces by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight of active compound.

The compounds are employed in a customary manner appropriate for the use forms.

When used against hygiene pests and pests of stored products, the active compounds are distinguished by an excellent residual action on wood and clay as well as by a good stability to alkali on limed substrates.

The following examples illustrate the present invention specifically. The present invention shall not be deemed to be limited to them alone.

PREPARATION EXAMPLES

Example 1

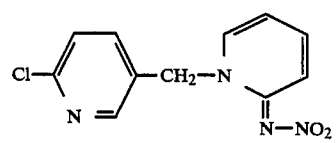

(Compound No. 1)

2-Chloro-5-chloromethylpyridine (3.24 g) and 2-nitraminopyridine (2.78 g) were dissolved in anhydrous ethanol (50 ml), and triethylamine (4.04 g) was added to the solution. The mixture was stirred at room temperature for a while. Then, it was heated under reflux conditions for 8 hours. The reaction mixture was cooled to room temperature, and poured into ice water. The precipitated crystals were collected by filtration, and recrystallized from ethanol to give pale yellow 1-(2-chloro-5-pyridylmethyl)-2-nitroimino-1,2-dihydropyridine (2.3 g) as the desired compound. mp. 209–212° C.

Example 2

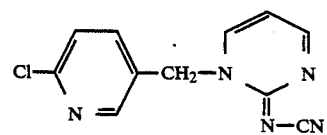

(Compound No. 25)

A mixture of 2-chloro-5-chloromethylpyridine (3.24 g), 2-cyanaminopyrimidine (2.4 g), anhydrous potassium carbonate (3.04 g) and acetonitrile (100 ml) was refluxed for 5 hours under stirring. About 50 ml of the acetonitrile were evaporated under reduced pressure, and the residue was poured into ice water. The precipitated crystals were collected by filtration, and recrystallized from ethanol to give 1-(2-chloro-5-pyridylmethyl)-2-cyanoimino-1,2-dihydropyridimidine (1.87 g) as colorless crystals. mp. 218°–220° C.

Table 1 lists compounds of this invention obtained by the same methods as described in Examples 1 and 2 together with the compounds obtained in Examples 1 and 2.

TABLE 1

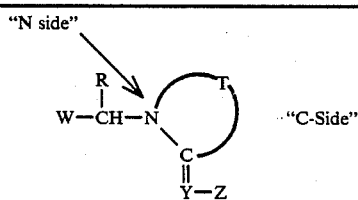

| Compound No. | W | R | N side  T  C side | Y | Z | |
|---|---|---|---|---|---|---|
| 1 | 6-chloropyridin-3-yl | H | —CH=CH—CH=CH— | =N— | NO$_2$ | mp. 209~212° C. |
| 2 | 6-chloropyridin-3-yl | H | —CH=C(CH$_3$)—CH=CH— | =N— | NO$_2$ | mp. 188~190° C. |
| 3 | 6-chloropyridin-3-yl | H | —CH=CH—CH=C(CH$_3$)— | =N— | NO$_2$ | $n_D^{20}$ 1.5939 |
| 4 | 6-chloropyridin-3-yl | H | —CH=C(Cl)—CH=CH— | =N— | NO$_2$ | mp. 84~85° C. |
| 5 | 6-chloropyridin-3-yl | H | —CH=C(Br)—CH=CH— | =N— | NO$_2$ | mp. 210~217° C. |
| 6 | 6-chloropyridin-3-yl | H | —CH=C(Br)—CH=C(Br)— | =N— | NO$_2$ | mp. 229~232° C. |
| 7 | 6-chloropyridin-3-yl | H | —CH=C(CF$_3$)—CH=CH— | =N— | NO$_2$ | mp. 159~160° C. |
| 8 | 3-methylisoxazol-5-yl | H | —CH=CH—CH=CH— | =N— | NO$_2$ | mp. 159~161° C. |
| 9 | 2-chlorothiazol-5-yl | H | —CH=CH—CH=CH— | =N— | NO$_2$ | mp. 87~88° C. |
| 10 | 6-chloropyridin-3-yl | H | —CH=CH—S— | =N— | NO$_2$ | mp. 219~220° C. |
| 11 | 6-chloropyridin-3-yl | H | —N=CH—S— | =N— | NO$_2$ | mp. 166~167° C. |

TABLE 1-continued

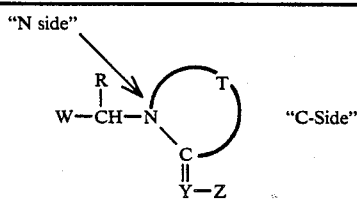

| Compound No. | W | R | N side  T  C side | Y | Z | |
|---|---|---|---|---|---|---|
| 12 | 6-chloropyridin-3-yl | H | $-N=\underset{\underset{CH_3}{\vert}}{C}-S-$ | =N— | NO$_2$ | mp. 180~183° C. |
| 13 | 6-chloropyridin-3-yl | H | $-N=\underset{\underset{C_2H_5}{\vert}}{C}-S-$ | =N— | NO$_2$ | mp. 167~170° C. |
| 14 | 6-chloropyridin-3-yl | H | $-N=\underset{\underset{CF_3}{\vert}}{C}-S-$ | =N— | NO$_2$ | mp. 178~180° C. |
| 15 | 6-chloropyridin-3-yl | H | $-CH=\underset{\underset{Cl}{\vert}}{C}-CH=N-$ | =N— | NO$_2$ | mp. 90~95° C. |
| 16 | 6-chloropyridin-3-yl | H | $-N=\underset{\underset{Cl}{\vert}}{C}-CH=CH-$ | =N— | NO$_2$ | $n_D^{20}$ 1.6335 |
| 17 | 3-methylisoxazol-5-yl | H | —CH=CH—S— | =N— | NO$_2$ | mp. 224~227° C. |
| 18 | 3-methylisoxazol-5-yl | H | $-N=\underset{\underset{CH_3}{\vert}}{C}-S-$ | =N— | NO$_2$ | mp. 137~140° C. |
| 19 | 2-chlorothiazol-5-yl | H | $-N=\underset{\underset{CH_3}{\vert}}{C}-S-$ | =N— | NO$_2$ | mp. 122~124° C. |
| 20 | 6-chloropyridin-3-yl | H | —CH=CH—CH=CH— | =N— | CN | mp. 184~186° C. |
| 21 | 6-chloropyridin-3-yl | H | $-CH=\underset{\underset{Cl}{\vert}}{C}-CH=CH-$ | =N— | CN | mp. 215~219° C. |

TABLE 1-continued

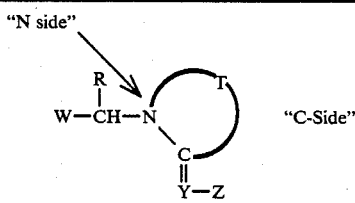

| Compound No. | W | R | N side T C side | Y | Z | |
|---|---|---|---|---|---|---|
| 22 | 2-Cl-pyridin-5-yl | H | -CH=C(Cl)-C(Cl)=C- | =N- | CN | |
| 23 | 2-Cl-pyridin-5-yl | H | -CH=CH-S- | =N- | CN | mp. 151~154° C. |
| 24 | 2-Cl-pyridin-5-yl | H | -N=CH-S- | =N- | CN | mp. 122-124° C. |
| 25 | 2-Cl-pyridin-5-yl | H | -CH=CH-CH=N- | =N- | CN | mp. 218~220° C. |
| 26 | 2-Cl-thiazol-5-yl | H | -CH=CH-CH=CH- | =N- | CN | mp. 218~219° C. |
| 27 | 2-CH$_3$-pyridin-5-yl | H | -CH=CH-CH=CH- | =N- | NO$_2$ | |
| 28 | 2-F-pyridin-5-yl | H | -CH=CH-CH=CH- | =N- | NO$_2$ | |
| 29 | 2-Cl-pyridin-5-yl | CH$_3$ | -CH=CH-CH=CH- | =N- | NO$_2$ | |
| 30 | 2-Br-pyridin-5-yl | H | -CH=CH-CH=CH- | =N- | NO$_2$ | |
| 31 | 1-CH$_3$-pyrazol-4-yl | H | -CH=CH-CH=CH- | =N- | NO$_2$ | |

TABLE 1-continued

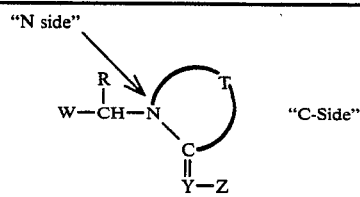

"N side" / "C-Side"

| Compound No. | W | R | N side T C side | Y | Z |
|---|---|---|---|---|---|
| 32 | iso-H₇C₃-pyrazolyl | H | —CH=CH—CH=CH— | =N— | NO₂ |
| 33 | H₃C-imidazolyl (NH) | H | —CH=CH—CH=CH— | =N— | NO₂ |
| 34 | Cl-pyrimidinyl | H | —CH=CH—CH=CH— | =N— | NO₂ |
| 35 | Cl-pyridazinyl | H | —CH=CH—CH=CH— | =N— | NO₂ |
| 36 | Cl-pyridyl | H | —CH=CH—O— | =N— | NO₂ |
| 37 | F₂HC-pyridyl | H | —CH=CH—S— | =N— | NO₂ |
| 38 | F-pyridyl | H | —CH=CH—CH=N— | =N— | NO₂ |
| 39 | F₃C-pyridyl | H | —N=C(Cl)—CH=CH— | =N— | NO₂ |
| 40 | F₃C-isoxazolyl | H | —CH=CH—S— | =N— | NO₂ |
| 41 | F-thiazolyl | H | —CH=CH—S— | =N— | NO₂ |

TABLE 1-continued

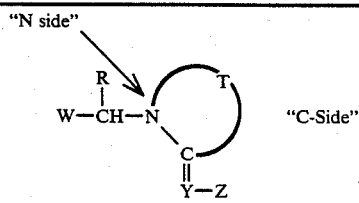

| Compound No. | W | R | N side T C side | Y | Z |
|---|---|---|---|---|---|
| 42 | 2-chloro-thiazol-5-yl | H | —CH=CH—S— | =N— | NO$_2$ |
| 43 | 1,2,3-thiadiazol-4-yl | H | —CH=CH—S— | =N— | NO$_2$ |
| 44 | 1,2,3-thiadiazol-5-yl | H | —CH=CH—S— | =N— | NO$_2$ |
| 45 | 5-chloro-pyrazin-2-yl | H | —CH=CH—S— | =N— | NO$_2$ |
| 46 | 5-methyl-pyrazin-2-yl | H | —CH=CH—NH— | =N— | NO$_2$ |
| 47 | 2-methyl-pyrimidin-5-yl | H | —CH=CH—CH=N— | =N— | NO$_2$ |
| 48 | pyridazin-4-yl | H | —CH=C(Cl)—CH=N— | =N— | NO$_2$ |
| 49 | 6-fluoro-pyridin-3-yl | H | —CH=CH—CH=CH— | =N— | CN |
| 50 | 6-chloro-pyridin-3-yl | CH$_3$ | —CH=CH—CH=CH— | =N— | CN |
| 51 | 2,3-dichloro-pyridin-5-yl | H | —CH=CH—CH=CH— | =N— | CN |
| 52 | 6-methyl-pyridin-3-yl | H | —CH=CH—CH=C(CH$_3$)— | =N— | CN |

TABLE 1-continued
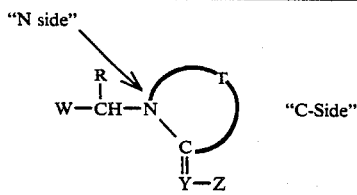
| Compound No. | W | R | N side T C side | Y | Z |
|---|---|---|---|---|---|
| 53 | H₃C-N(pyrazole) | H | —CH=CH—CH=CH— | =N— | CN |
| 54 | Cl-(isoxazole, N—O) | H | —CH=CH—CH=CH— | =N— | CN |
| 55 | H₃C-(isoxazole, N—O) | H | —CH=CH—CH=CH— | =N— | CN |
| 56 | (isoxazole N—O) | H | —CH=CH—CH=CH— | =N— | CN |
| 57 | Cl-(thiadiazole N—N, S) | H | —CH=CH—CH=CH— | =N— | CN |
| 58 | H₃C-(oxadiazole N—N, O) | H | —CH=CH—CH=CH— | =N— | CN |
| 59 | H₃C-(pyrazine) | H | —CH=CH—CH=CH— | =N— | CN |
| 60 | Cl-(pyrimidine) | H | —CH=CH—CH=CH— | =N— | CN |
| 61 | Cl-(isoxazole N—O) | H | —CH=CH—S— | =N— | CN |

TABLE 1-continued

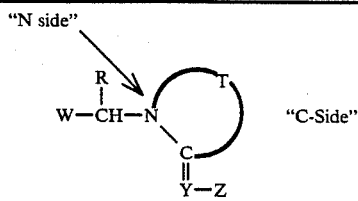

| Compound No. | W | R | N side T C side | Y | Z |
|---|---|---|---|---|---|
| 62 | 2-chloro-thiazol-5-yl | H | —CH=CH—S— | =N— | CN |
| 63 | 1,2,3-thiadiazol-4-yl | H | —CH=CH—S— | =N— | CN |
| 64 | 3-methyl-isoxazol-5-yl | H | —CH=CH—CH=N— | =N— | CN |
| 65 | 2-methyl-thiazol-5-yl | H | —CH(CH₃)—CH=C(CH₃)—N— | =N— | CN |
| 66 | 5-methyl-pyrazin-2-yl | H | —CH=CH—S— | =N— | CN |
| 67 | 2-methyl-pyrimidin-5-yl | H | —CH=CH—S— | =N— | CN |
| 68 | 2-chloro-pyrazin-5-yl | H | —CH=CH—CH=N— | =N— | CN |
| 69 | 6-chloro-pyridin-3-yl | H | —CH=CH—CH=CH— | =CH— | NO₂ |
| 70 | 6-methyl-pyridin-3-yl | H | —CH=CH—CH=CH— | =CH— | NO₂ |
| 71 | 3-methyl-isoxazol-5-yl | H | —CH=CH—CH=CH— | =CH— | NO₂ |

Note: structures in column W are drawn as heterocyclic rings; compound 65 T/C side: —CH=CH—C(CH₃)=N— with CH₃ substituents as shown.

TABLE 1-continued

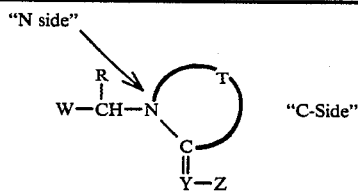

| Compound No. | W | R | N side | T | C side | Y | Z |
|---|---|---|---|---|---|---|---|
| 72 | 2-chloro-thiazol-5-yl | H | —CH=CH— | | —CH=CH— | =CH— | NO$_2$ |
| 73 | 2-methyl-pyrazin-5-yl | H | —CH=CH— | | —CH=CH— | =CH— | NO$_2$ |
| 74 | 6-chloro-pyridin-3-yl | H | —CH=CH— | | —CH=N— | =CH— | NO$_2$ |
| 75 | 6-chloro-pyridin-3-yl | H | —CH=N— | | —CH=CH— | =CH— | NO$_2$ |
| 76 | 6-methyl-pyridin-3-yl | H | —O— | | N=CH— | =CH— | NO$_2$ |
| 77 | 2-chloro-thiazol-5-yl | H | —CH=N— | | —CH=CH— | =CH— | NO$_2$ |
| 78 | 6-chloro-pyridin-3-yl | H | —CH=CH—S | | | =CH— | NO$_2$ |
| 79 | 2-chloro-thiazol-5-yl | H | —CH=CH—S— | | | =CH— | NO$_2$ |
| 80 | 6-chloro-pyridin-3-yl | H | —CH=CH—NH— | | | =CH— | NO$_2$ |
| 81 | 6-chloro-pyridin-3-yl | H | —CH=CH— | | —CH=CH— | =CH— | CN |

TABLE 1-continued
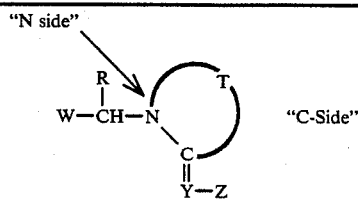
| Compound No. | W | R | N side T C side | Y | Z | |
|---|---|---|---|---|---|---|
| 82 | 6-Cl-pyridin-3-yl | H | —CH=CH—CH=N— | =CH— | CN | |
| 83 | 6-Br-pyridin-3-yl | H | —CH=CH—CH=N— | =CH— | CN | |
| 84 | 1,2,5-thiadiazol-3-yl | H | —CH=CH—CH=N— | =CH— | CN | |
| 85 | 6-Cl-pyridin-3-yl | H | —CH=CH—NH— | ·=CN— | CN | |
| 86 | 2-methylpyrazin-5-yl | H | —CH₂—N=CH— | =CH— | CN | |
| 87 | 6-Cl-pyridin-3-yl | H | —CH=CH—S— | =CH— | CN | |
| 88 | 6-Cl-pyridin-3-yl | H | —CH=CH—NH— | =N— | NO₂ | mp. 186–189° C. |
| 89 | 2-Cl-thiazol-5-yl | H | —CH=CH—NH— | =N— | NO₂ | mp. 156–157° C. |
Biological tests
Comparative Compounds
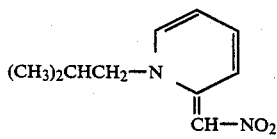
A-1:
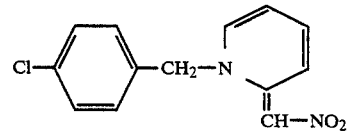
A-2:
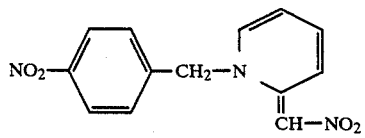
A-3:

(A-1, A-2 and A-3: the compounds described in Japanese Laid-Open Patent Publication No. 29,570/1975)

B-1:

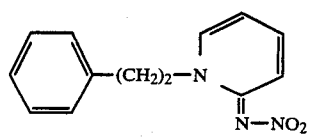

(the compound described in J. Med. Chem., 1971, vol. 14, pages 988-990)

Example 8 (biological test)

Test on *Nephotettix cincticeps* having resistance to organophosphorus agents:

Preparation of a test chemical

Solvent: 3 parts by weight of xylene
Emulsifier: 1 part by weight of polyoxyethylene alkyl phenyl ether To form a suitable test chemical preparation, 1 part by weight of the active compound was mixed with the aforesaid amount of the solvent containing the aforesaid amount of the emulsifier. The mixture was diluted with water to a predetermined concentration.

Testing method

Onto rice plants, about 10 cm tall, planted in pots each having a diameter of 12 cm 10 ml per pot of the water-dilution of the active compound was sprayed in a predetermined concentration prepared above. The sprayed chemical was dried, and a wire net having a diameter of 7 cm and a height of 14 cm was put over the rice plants, and 30 female imagoes of *Nephotettix cincticeps* showing resistance to organophosphorus agents were released into the net. The pots were each placed in a constant temperature chamber and the number of dead insects was examined 24 hours later, and the kill ratio was calculated.

In this test compounds 1,2,8,10,20,23,25,26 exhibited a kill ratio of 100% at a concentration of 8 ppm of the active ingredient, whereas the comparison compounds A-1, A-3 and B-1 showed no effect at 40 ppm and comparison compound A-2 showed no effect at a concentration of 8 ppm.

Example 4 (biological test)

Test on planthoppers:

Testing procedure

Water dilution in a predetermined concentration of each active compound, prepared as in Example 3, was sprayed in an amount of 10 ml per pot onto rice plants, about 10 cm all, grown in pots each having a diameter of 12 cm. After drying the sprayed chemical, a wire net having a diameter of 7 cm and a height of 14 cm was put over each pot, and 30 female imagoes of *Nilaparvata lugens* were released into the net. The pots were placed in an incubator, and the number of dead insects was examined two days later. The kill ratio was calculated.

By the same procedure as above, the kill ratios on *Sogatella furcifera* and organophorphorus-resistant *Laodelphax striatellus* were calculated.

In this test for instance compounds 1, 2, 8 and 10 according to the present patent application exhibited a kill ratio of 100% against N. lugens, L. striatellus and S. furcifera at a concentration of 40 ppm of the active ingredient, whereas the comparison compounds A-1, A-2, A-3 and B-1 were either ineffective or considerably less effective in the above mentioned test systems.

Example 5 (biological test)

Test on *Myzus persicae* (green peach aphids) having resistance to organophosphorus agents and carbamate agents:

Testing method

Green peach aphids which had been bred were inoculated on eggplant seedlings (black elongated eggplants), about 20 cm tall, grown in unglazed pots having a diameter of 15 cm (about 200 aphids per seedling). One day after the inoculation, a water dilution of each active compound at a predetermined concentration prepared as in Example 3 was sprayed in a sufficient amount onto the plants using a spray gun. After the spraying, the pots were left to stand in a greenhouse at 28° C. Twenty-four hours after the spraying, the kill ratio was calculated. For each compound, the test was carried out through two replicates.

In this test system for instance compounds 1, 2, 8 and 10 according to the present application exhibited a kill ratio of 100% at a concentration of 200 ppm of the active ingredient, whereas the comparison compounds A-1, A-2, A-3 and B-1 were either ineffective or considerably less effective against *Myzus persicae*.

It will be understood that the specification and examples are illustrative but not limitative of the present invention and that other embodiments within the spirit and scope of the invention will suggest themselves to those skilled in the art.

We claim:

1. A heterocyclic compound of the formula

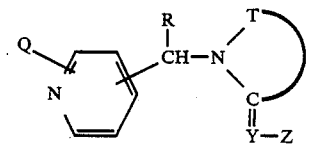

wherein
Q is at least one substituent selected from halogen atoms, $C_1$-$C_4$ alkyl groups optionally substituted by halogen, $C_1$-$C_4$ alkoxy groups optionally substituted by halogen, $C_2$-$C_4$ alkenyl groups optionally substituted by halogen, $C_1$-$C_4$ alkylsulfinyl groups, $C_1$-$C_4$ alkylsulfonyl groups and $C_3$-$C_4$ alkynyl groups,
R represents a hydrogen atom or a methyl group,
Y represents =N— or =CH—,
Z represents a nitro group or a cyano group, and
T represents —CH=CH—S—, wherein the S is attached to

said 5-membered unsaturated heterocyclic ring being optionally substituted by at least one of halogen atoms and $C_1$-$C_4$ alkyl groups optionally substituted by halogen.

2. A compound according to claim 1, wherein such compound is 3-(2-chloro-5-pyridylmethyl)-2-nitroimino-4-thiazoline of the formula

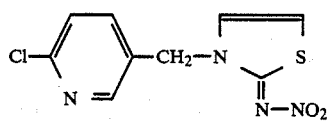
3. An insecticidal composition comprising an insecticidally effective amount of a heterocyclic compound according to claim 1 and a diluent.
4. A method of combating insects which comprises applying to such insects or to an insect habitat an insecticidally effective amount of a heterocyclic compound according to claim 1.
* * * * *